United States Patent
Ellis-Grosse et al.

(10) Patent No.: US 6,656,931 B2
(45) Date of Patent: Dec. 2, 2003

(54) VASOPRESSIN ANTAGONIST AND DIURETIC COMBINATION

(75) Inventors: Evelyn Ellis-Grosse, Downingtown, PA (US); Gayle P. Orczyk, Berwyn, PA (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/162,451

(22) Filed: Jun. 4, 2002

(65) Prior Publication Data

US 2003/0069227 A1 Apr. 10, 2003

Related U.S. Application Data

(62) Division of application No. 09/669,461, filed on Sep. 25, 2000, now Pat. No. 6,420,358.
(60) Provisional application No. 60/198,237, filed on Sep. 27, 1999, now abandoned.

(51) Int. Cl.[7] .................. A61K 31/55; A61K 31/34; A61K 31/495; A61K 31/505; A61K 31/405
(52) U.S. Cl. .................. 514/220; 514/471; 514/249; 514/255.06; 514/259; 514/416; 514/562; 514/571
(58) Field of Search ................... 514/220, 471, 514/249, 255.06, 259, 416, 461, 562, 571

(56) References Cited

U.S. PATENT DOCUMENTS

| | | |
|---|---|---|
| 4,578,391 A | 3/1986 | Kawata et al. |
| 4,620,974 A | 11/1986 | Hersh et al. |
| 4,744,988 A | 5/1988 | Brox |
| 5,516,774 A | 5/1996 | Albright et al. |
| 5,641,512 A | 6/1997 | Cimiluca |

FOREIGN PATENT DOCUMENTS

| | | |
|---|---|---|
| EP | 0815 854 A1 | 1/1998 |
| WO | WO 95/19579 | 7/1995 |
| WO | WO 96/40071 | 12/1996 |
| WO | WO 96/41622 | 12/1996 |

OTHER PUBLICATIONS

Medline AN 1998001744, Selvaag, Arzneimittel–Forschung, Sep. 1997 47 (9) 1031–4 abstract.*
Goodman and Gilman, Pharmacological Basis of Therapeutics, 1975, pp. 829 (Table 39–3), 833.*
Merck Index, 1983, p. 60, #406, p. 204, #1452.*
Remington's Pharmaceutical Sciences, 1975, pp. 867–872.*
Shah et al., Bull. Tech/Gattefosse Rep., 1996, 89, 27–38.
Chan et al., Vasopressin and Oxytocin, 439–443, 1998.
Swan et al., J. Am. Soc. of Nephrology, 10, p. 124, Sep. 1999.

* cited by examiner

*Primary Examiner*—Rebecca Cook
(74) *Attorney, Agent, or Firm*—Joseph M. Mazzarese

(57) ABSTRACT

This invention provides methods of increasing urine flow in humans while minimizing the loss of electrolytes or ions, the methods comprising administering to a human in need thereof a combination of N-[4-(5H-pyrrolo[2,1-c][1,4]benzodiazepin-10(11H)ylcarbonyl)-3-chlorophenyl]-5-fluoro-2-methylbenzamide (or a pharmaceutically acceptable salt thereof), also known as VPA-985, and one or more diuretic agents, as well as pharmaceutical compositions and kits or packages for such combinations.

9 Claims, No Drawings

VASOPRESSIN ANTAGONIST AND DIURETIC COMBINATION

This application is a division of Ser. No. 09/669,461 filed Sep. 25, 2000 now U.S. Pat. No. 6,420,358, which claims the benefit of U.S. Provisional Application No. 60/198,237, which was converted from U.S. patent application Ser. No. 09/406,658, filed Sep. 27, 1999, now abandoned, pursuant to a petition filed under 37 C.F.R. 1.53(c)(2)(i).

This invention relates to new methods of increasing urine flow in humans while controlling the loss of electrolytes, the method comprising administering N-[4-(5H-pyrrolo[2,1-c][1,4]benzodiazepin-10(11H)ylcarbonyl)-3-chlorophenyl]-5-fluoro-2-methylbenzamide (or a pharmaceutically acceptable salt thereof) and a diuretic, such as furosemide. Particularly, this invention provides useful means for removing excess water, such as in the case of congestive heart failure, while maintaining a desirable blood osmolality in the recipient.

BACKGROUND OF THE INVENTION

The art describes many methods of producing liquid or semi-solid encapsulated pharmaceutical formulations. In Bull. Tech./Gattefosse Rep. (1996), 89, 27–38, authors Shah et al. describe hard gelatin capsule technology, particularly for use in enhancing the bioavailability of poorly soluble or poorly absorbed drugs.

U.S. Pat. No. 4,620,974 (Hersh et al.) teaches a hard gelatin capsule comprising a telescoping two-piece cap with a lubricant comprising a polyethylene glycol of a molecular weight between about 200 and about 900 present in admixture with the composition at a concentration of from about 0.5 to about 25 weight percent.

WO 96/40071 (Lamberti) discloses methods and devices for producing minimal volume capsules. WO 96/41622 (Tanner et al.) teaches suspensions suitable for encapsulation in gelatin capsules, particularly including a solid phase of solid particles and a liquid phase capable of suspending the solid phase.

U.S. Pat. No. 5,641,512 (Cimiluca) teaches soft gelatin encapsulated analgesics in which the shell contains a xanthine derivative, such as caffeine.

EP 0 815 854 A1 discloses a substantially translucent, semi-solid fill material for a soft gelatin capsule, the semi-solid material being sufficiently viscous that it cannot be expelled from the capsule with a syringe at room temperature.

U.S. Pat. No. 4,744,988 (Brox) teaches soft gelatin capsules comprising a shell of gelatin, a softener and a filling of a polyethylene glycol and a low polyhydric alcohol and at least one active substance, characterized in that the shell contains 4 to 40 percent sorbital or sorbitanes, at least half of the weight of polyethylene glycol used is a polyethylene glycol having a mean molecular weight of 600, and the capsule filling comprises up to 20% by weight of glycerol and/or 1,2-propylene glycol.

WO 95/19579 (Dhabhar) teaches a process for solubilizing difficulty soluble pharmaceutical agents in a mixture of polyethylene glycol and propylene glycol by using a polyvinylpyrrolidone with a specific viscosity average molecular weight of from about 5,000 to about 25,000.

SUMMARY OF THE INVENTION

Diuretics are commonly used in the treatment of hypertension and management of edema, such as with congestive heart failure. Of significant concern in such treatments is the loss of ions or electrolytes, particularly including sodium and potassium, with the increased volume of urine.

This invention provides methods of increasing urine flow in humans while minimizing, inhibiting or limiting loss of electrolytes or ions, the methods comprising administering to a human in need thereof a combination of N-[4-(5H-pyrrolo[2,1-c][1,4]benzodiazepin-10(11H)ylcarbonyl)-3-chlorophenyl]-5-fluoro-2-methyl-benzamide (or a pharmaceutically acceptable salt thereof), also known as VPA-985, and one or more diuretic agents. The active agents of this invention are preferably given orally, but may be administered intravenously or parenterally, as needed.

This invention may also be seen as an improved method of increasing urine flow in a human by administering one or more diuretics to the human, the improvement comprising administering in conjunction with the diuretic a pharmacologically effective amount of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof. Similarly, this invention may be characterized as an improved method of retaining electrolytes or ions in the blood during diuretic administration, the method comprising the coadministration of VPA-985 with the diuretic.

N-[4-(5H-pyrrolo[2,1-c][1,4]benzodiazepin-10(11H)ylcarbonyl)-3-chlorophenyl]-5-fluoro-2-methylbenzamide can be seen as Example 482 in U.S. Pat. No. 5,516,774, which is incorporated herein by reference and fully explains the production of VPA-985 and its salts, which has the structure:

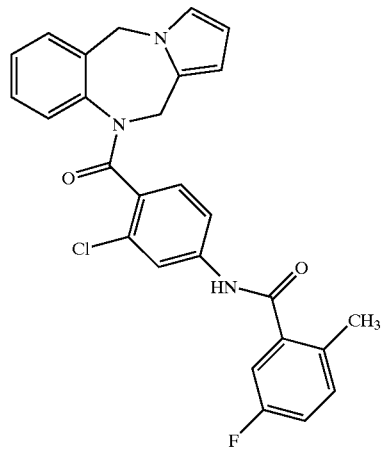

Preferably, this active compound is formulated with a carrier system herein and encapsulated for oral administration by methods known in the art, preferably with a soft or hard gelatin capsule.

Among the diuretic agents useful for the combination regimens of this invention are thiazide and related sulfonamide diuretics bendroflumethiazide, benzthiazide, chlorothiazide, chlorthalidone, cyclothiazide, hydrochlorothiazide, hydroflumethiazide, indapamide, methylclothiazide, metolazone, polythiazide, quinethazone and thrichlormethiazide. Also useful are potassium-sparing diuretics, such as amiloride, spironolactone and triamterene. Among the more preferred diuretics for use with this invention are the Loop diuretics, such as bumetanide, ethacrynic acid, ethacrynate sodium, and furosemide (sold under the Lasix® tradename, Hoechst Marion Roussel). The diuretics herein are known in the art and can be administered in the fashion and at the concentrations known in the art.

In one embodiment of the present invention N-[4-(5H-pyrrolo[2,1-c][1,4]benzodiazepin-10(11H)ylcarbonyl)-3-chlorophenyl]-5-fluoro-2-methyl-benzamide, or a pharmaceutically acceptable salt is administered to the recipient at a daily dose of from about 25 mg to about 400 mg, preferably from about 40 mg to about 200 mg, most preferably between about 50 mg and about 150 mg, in conjunction with furosemide administration at a daily concentration of from about 20 mg to about 100 mg, more preferably from about 20 mg to about 80 mg. The doses of this combination regimen are preferably administered at the same time(s) per day and may be administered once per day or divided into two or more doses, as required for the desired urine output.

Joint administrations with ethacrynic acid (tablets available under the tradename Edecrin®, Merck & Co., Inc.) are preferably at a daily dose range of from about 25 mg to 200 mg per day, more preferably at a daily dose range of from about 50 mg to about 100 mg per day if desirable urine output is maintained.

Bumetanide administrations with this invention are preferably maintained at a daily dose range of from about 0.25 mg to about 5 mg. Spironolactone may be combined in formulations of this invention preferably at a daily dose range of from about 50 mg to 400 mg/day, more preferably at a range of from about 100 mg to 300 mg/day, more preferably at a range of from 150 mg to about 250 mg/day. Hydrochlorothiazide may be administered in these formulations at a dose range of from about 10 mg to about 100 mg/day, preferably from about 25 to about 50 mg/day.

Coadministration of VPA-985 and a diuretic provides an additive urine output over either compound alone and provides retention of ions or electrolytes and osmolality maintenance over the administration of diuretics, alone.

VPA-985 formulations useful with this invention may comprise (by % w/w):

a) from about 1% to about 20% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof, preferably from about 5% to about 16% of this active ingredient;

b) from about 1% to about 15% of a surfactant component, preferably from about 5% to about 10% of the surfactant component;

c) from about 50% to about 80% of a component of one or more polyethylene glycols (PEG), preferably from about 55% to about 70% of one or more polyethylene glycols; and d) from about 1% to about 20%, preferably from about 5% to about 15% and more preferably between about 8% and about 12%, of a component of:
  i) one or more sucrose fatty acid esters; or
  ii) a polyvinylpyrrolidone (PVP) with a K value between about 15 and 90, preferably with a K value of from about 17 as defined in USP/NF; or
  iii) a combination of one or more sucrose fatty acid esters and a PVP, as defined above.

The polyethylene glycol component may be comprised of one or more PEG polymers, preferably commercially available PEG polymers between PEG 200 and PEG 4,000, i.e. those PEG polymers having an average molecular weight between about 190 and about 4800. More preferred are PEG polymers between average molecular weights of from about 190 to about 3450, most preferably between about 400 and 1540. Among the preferred PEG polymers are PEG 400, having an average molecular weight between about 380 and about 420, and PEG 1,000, having an average molecular weight between about 950 and about 1050. The ratio of high and low molecular weight PEG species within the PEG component is preferably from about 2.5:1 to about 1:2.5, more preferably about 1:1. As an example, a preferred blend of PEG polymers within this invention would include a 1:1 blend of PEG 400 and PEG 1000. It may be preferable to choose a mixture of PEG components which will have a melting point at or near the physiological temperature of the mammal to receive the formulation. Mixtures of final components which have a viscosity range of from about 140 to about 1500 centipoise at 37•C may be preferred, more preferably a range of from 300 to about 800 centipoise at 37•C.

The surfactants that may be used with the present formulations include, but not limited to, polysorbate 20 (polyoxyethylene 20 sorbitan monolaurate), Polysorbate 60, Polysorbate 40, polysorbate 80, Span 80 Sorbitan Oleate, a product of ICI Americas, Wilmington, Del., polysorbate 81, polysorbate 85, polysorbate 120, bile acids and salts defined by Martindale The Extra Pharmacopoeia Thirtieth Edition on page 1341–1342 such as Sodium taurocholates, Sodium deoxytaurocholates, Chenodeoxycholic acid, and ursodeoxycholic acid, and pluronic or poloxamers such as Pluronic F68, Pluronic L44, Pluronic L101, or combinations of one or more of the above. Polysorbate 80, by itself or in combination with one or more other surfactants, is preferred for use with this invention.

The sucrose fatty acid esters useful with this invention include those commercially available and art recognized esters useful for orally administered pharmaceutical compositions, including monoesters, diesters and triesters of sucrose, or mixtures or blends thereof. Specific examples of esters useful with this invention are sucrose monolaurate, sucrose monomyristate, sucrose monopalminate, sucrose monostearate, sucrose distearate, sucrose tristearate, sucrose trimyristate, and sucrose tripalmitate, or combinations thereof.

In addition to these components, other enhancing or protective pharmaceutically acceptable antioxidants or preservatives may be added to the compositions of this invention, preferably in an amount from about 0.1% to about 4.0% by weight of the composition, more preferably from about 0.1% to about 3.0%. Examples may include ascorbyl palmitate, benzyl alcohol, butylated hydroxyanisole (BHA), butylated hydroxytoluene (BHT), etc. Examples of these components in the present formulations would include BHA at a concentration from about 0.3% to about 2.5% (% w/w) and BHT at a concentration from about 0.005% to about 0.15% (% w/w), preferably with a mixture of BHA and BHT within these ranges.

A further formulation utilizing one or more of these antioxidants or preservatives comprises:

a) from about 1% to about 20% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof, preferably from about 5% to about 16% of this active ingredient;

b) from about 1% to about 18% of a surfactant component, preferably from about 5% to about 15% of the surfactant component, more preferably from about 8 to about 12% of the surfactant component;

c) from about 50% to about 80% of a component of one or more polyethylene glycols (PEG), preferably from about 55% to about 70% of one or more polyethylene glycols;

d) from about 1% to about 20%, preferably about 5% to about 15%, of one or more sucrose fatty acid esters or polyvinylpyrrolidone (PVP) with a K value between about 15 and 90, preferably with a K value of from about 17 as defined in USP/NF; and e) from about 0.1% to about 4%, preferably from about 0.1% to about 3%, of one or more preservatives or antioxidants, for example from about 0.3% to about 2.5% (% w/w) BHA and/or from about 0.005% to about 0.15% (% w/w) BHT.

One preferred embodiment of this invention provides a pharmaceutical formulation comprising:

a) from about 5% to about 16% of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof;

b) from about 5% to about 10% of a surfactant component;

c) a component of from about 55% to about 70% of one or more polyethylene glycols;

d) from about 5% to about 15% of polyvinylpyrrolidone (PVP) with a K value between about 15 and 90, preferably with a K value of from about 17 as defined in USP/NF; and e) from about 0.3% to about 2.5% (% w/w) BHA and from about 0.005% to about 0.15% (% w/w) BHT.

Preferably, the formulations of this invention are enclosed in a sealed enclosure after manufacture, such as soft or hard gelatin capsules. The formulations of this invention may be created as a liquid or semi-liquid formulation and introduced into a capsule. Similarly, using an acceptable range of components and/or temperatures, the formulation may be made as a gel or solid prior to encapsulation.

It will be understood by those skilled in the art that the volume of carrier may be adjusted depending upon the mass of active pharmaceutical agent to be incorporated therein, such as within a range of from about 1 mg to about 1,000 mg per dose unit, preferably an encapsulated oral dose unit. Using the percent ranges for the various components described above for the carrier systems, the VPA-985 pharmaceutical compositions of this invention may be produced by the steps of:

a) combining, preferably with mixing or stirring, the PEG 400, PEG 1000 and Polysorbate 80 components to create a first carrier mixture;

b) raising the temperature of the first carrier mixture to a range of from about 75° C. to about 95° C., preferably from about 80° C. to about 90° C.;

c) adding to the first carrier mixture the BHA and BHT components to create a second carrier mixture, which is then stirred or otherwise mixed until the second carrier mixture is a clear solution;

d) adding the active pharmacological agent or drug component to create a first pharmaceutical composition mixture;

e) stirring the first pharmaceutical composition mixture, preferably with heating, until the first pharmaceutical composition mixture is clear, preferably at a temperature from about 115° C. to about 170° C., more preferably from about 130° C. to about 150° C., most preferably at a temperature from about 135° C. to about 145° C.;

f) cooling the first pharmaceutical composition, if necessary, to a temperature of from about 75° C. to about 95° C., preferably from about 80° C. to about 90° C.;

g) adding the amount of povidone to create a final pharmaceutical composition mixture, with stirring, until the final pharmaceutical composition mixture is clear.

In a further embodiment of this invention, the process above further comprises an additional step of encapsulating the final pharmaceutical composition mixture, such as with a soft gelatin capsule or with a hard gelatin capsule and band sealing. It will be understood that, depending upon the physical and chemical characteristics of the active pharmaceutical ingredient, the processes above may be completed under an inert atmosphere, under vacuum, in the absence of light, with filtration between some or all of the steps, or in conjunction with other process conditions known to those skilled in the art.

These formulations may comprise, for example, a non-limiting amount of N-[4-(5H-pyrrolo[2,1-c][1,4]benzodiazepin-10(11H)ylcarbonyl)-3-chlorophenyl]-5-fluoro-2-methylbenzamide (VPA-985), or a pharmaceutically acceptable salt thereof, at a concentration of from about 1 mg to about 2,000 mg per unit dose, preferably from about 10 to about 1,000 mg/unit dose, more preferably from about 25 to about 500 mg/unit dose, in a carrier or excipient system of this invention, as described above.

A specific process of this invention comprises producing an orally administerable pharmaceutical formulation containing the steps of:

a) combining, preferably with mixing or stirring, the PEG 400, PEG 1000 and Polysorbate 80 components to create a first carrier mixture;

b) raising the temperature of the first carrier mixture to a range of from about 75° C. to about 95° C., preferably from about 80° C. to about 90° C.;

c) adding to the first carrier mixture the BHA and BHT components to create a second carrier mixture, which is then stirred or otherwise mixed until the second carrier mixture is a clear solution;

d) adding an amount of VPA-985, or a pharmaceutically acceptable salt thereof, to create a first pharmaceutical composition mixture;

e) stirring the first pharmaceutical composition mixture, preferably with heating, until the first pharmaceutical composition mixture is clear, preferably at a temperature from about 115° C. to about 17° C., more preferably from about 130° C. to about 150° C., most preferably at a temperature from about 135° C. to about 145° C.;

f) cooling the first pharmaceutical composition, if necessary, to a temperature of from about 75° C. to about 95° C., preferably from about 80° C. to about 90° C.;

g) adding the amount of povidone to create a final pharmaceutical composition mixture, with stirring, until the final pharmaceutical composition mixture is clear.

Preferably, this reaction is conducted under a nitrogen atmosphere and the final pharmaceutical composition mixture is then filtered, such as through an 80 mesh screen, prior to encapsulation or coating, more preferably in a soft or hard gelatin capsule. For uniformity of the final composition, this process may be completed in two or more batches which are then combined with additional mixing to create a final mass batch of the formulation prior to encapsulating or coating. During encapsulation, it may be preferable to maintain the formulation and conduct the encapsulation under a nitrogen atmosphere at a temperature of from about 35° C. to about 50° C., more preferably at a temperature of from about 40° C. to about 45° C.

As a specific industrially applicable batch of a formulation herein for the production of 125,000 capsules of 100 mg doses of N-[4-(5H-pyrrolo[2,1-c][1,4]benzodiazepin-10 (11H)ylcarbonyl)-3-chlorophenyl]-5-fluoro-2-methyl-benzamide, or a pharmaceutically acceptable salt thereof (cited below as "Active Ingredient"), can be produced using the amounts of components listed below:

| Component | (% W/W) | Per Capsule (mg) | Total per 125,000 Capsules (kg) |
|---|---|---|---|
| Active Ingredient | 15.3846 | 100 | 12.5 |
| PEG 1000 | 28.9769 | 188.35 | 23.55 |
| Povidone USP K-17 | 10.00 | 65.00 | 8.125 |
| Polysorbate 80, NF | 9.4446 | 61.39 | 7.678 |
| BHT, NF | 0.0815 | 0.53 | 0.0665 |
| BHA, NF | 0.8185 | 5.32 | 0.6650 |
| PEG 400, NF | 35.2938 | 229.41 | 28.62 |
| Total | 100.00 | 650.00 | 80.5895 |

The beneficial results of this invention in humans can be seen by comparing the results in the rat and human studies of joint VPA-985 and furosemide, below.

Rat Study

NaCl reabsorption in the thick ascending limb of the Loop of Henle (TALH) creates free water that is reabsorbed in the collecting duct in the presence of vasopressin. To determine whether inhibition of TALH NaCl reabsorption blunts the aquaresis caused by inhibition of vasopressin-induced water reabsorption under hydropenic conditions, a combination of submaxial doses of VPA-985 (V), a vasopressin $V_2$ receptor antagonist, and furosemide (F), an inhibitor of TALH NaCl reabsorption, on renal function was studied in anesthetized rats. Either V (3 mg/kg), F (5 mg/kg), both V and F (V/F) or the vehicles were administered intraduodenally. One-hour clearances with midpoint blood samples were performed before and for 3 hours after compound administration. Both V and F caused similar increases in urine flow rate (5.26±1.13 to 19.51±3.80 and 3.74±0.18 to 17.02±4.86 µl/min, respectively). The combination did not have additive effect (V/F 4.03±0.15 to 24.7±6.05 µl/min). V and F decreased urine osmolality to a similar extent (V 1456±166 to 571±145, F 1515±96 to 699±69 mOsm/kg) while the combination caused a slightly larger decrease (1507±84 to 396±31 mOsm/kg). V caused a similar aquaresis in the presence and absence of F, as indicated by similar increases in free water clearance (V −17.31±1.84 to −6.96±5.17 and V/F −16.48±1.04 to 4.89±1.58 µl/min). F caused a similar natriuresis in the presence and absence of V. $Na^+$ excretion was increased from 0.09±0.02 to 1.77±0.60 with F and from 0.10±0.02 to 1.11±0.43 µEq/min with V/F. V alone caused a much smaller increase in $Na^+$ excretion (0.10±0.02 to 0.67±0.34 µEq/min). In all groups, mean arterial pressure (MAP) decreased from baseline values of 103–109 to 90–92 mmHg during the third hour. Glomerular filtration rate (GFR) was decreased during the $3^{rd}$ hour in all groups, consistent with the decreased MAP. In the drug-treated groups, GFR also decreased during the $2^{nd}$ hour (F 1.87±0.15 to 1.61±0.20 ml/in, V 2.04±0.15 to 1.70±0.11, V/F 2.13±0.09 to 1.38±0.09), possibly due to stimulation of the renin-angiotensin system by anesthesia-induced sympathetic activation, repeated blood sampling and increases in distal tubular flow rate. In this study, inhibition of NaCl reabsorption in the TALH by a submaximal dose of furosemide did not decrease the aquaretic effect of a submaximal dose of VPA-985, indicating little interaction between TALH NaCl reabsorption and vasopressin-induced water reabsorption.

Human Study

A randomized, 3-period crossover designed, single dose drug interaction study was conducted in healthy men to evaluate the potential pharmacodynamic and pharmacokinetic interaction between VPA-985 and furosemide in 12 healthy men. The study lasted approximately 30 days, and included a pre-enrollment evaluation of up to 2 weeks before dose administration, and three 2-day (2-night) confinement periods. The doses were separated by at least a 1 week interval. The clinical portion of the study was completed in approximately 2 months.

The study drugs were a single oral dose of VPA-985 75-mg suspension, furosemide 40-mg tablet, and a VPA-985 75-mg suspension with a furosemide 40-mg tablet. The VPA-985 suspension (25 mg and 50 mg powder reconstituted) was administered in 150 mL of Sprite® brand lemon-lime soda (a product of The Coca-Cola Company) followed by 100 mL of room-temperature water (250 mL of fluid total). Furosemide (40 mg tablets) was administered with 250 mL of room temperature water. When the 2 medications were administered together, furosemide was administered with the 100 mL of room temperature water, thereby assuring that all doses were administered with a total of 250 mL of fluid.

Pharmacokinetic and pharmacodynamic data for both VPA-985 and furosemide were analyzed by using model-independent methods. Areas under concentration-time curves($AUC_T$) (AUC) and AUC truncated at the last observed concentration ($C_T$)$AUC_T$) were determined by using the linear/log trapezoidal method. Statistical comparisons were made using by an analysis of variance (ANOVA). Confidence limits (90%) for pharmacokinetic parameters were constructed on a log scale using the two one-sided tests procedure. An interaction was judged to be significant if a 35% difference was detected between either single agent and the two drugs administered concomitantly.

VPA-985 was rapidly absorbed after oral administration with a mean time of peak concentration ($t_{max}$) of less than 1 hour. Mean values for peak concentration ($C_{max}$) and AUC were 617 ng/mL and 968 ng-h/mL, respectively. After oral administration, furosemide was rapidly absorbed with a mean $C_{max}$ of 1.3 ng/mL occurring within 2 h. Mean AUC and CLr values for furosemide were 2.62 ng-h/mL and 0.08 L/h/kg, respectively. Administration of VPA-985 with furosemide resulted in no differences in $C_{max}$, or AUCs as compared to VPA-985 alone. After coadministration with VPA-985, no difference was observed in the amount of furosemide recovered from urine (Ut), CLr, or AUC. A significant decrease in mean $C_{max}$ to 1.21 ng/mL was observed and the resulting 90% confidence interval for the ratio of $C_{max}$ geometric means was 64% to 136% which exceeded the predetermined range. The power associated with detecting a 35% difference in $C_{max}$ was low (12%). In addition, the $C_{max}$ for furosemide with VPA-985 was less than 10% smaller than with furosemide alone. For these reasons, there does not appear to be a clinically significant effect of VPA-985 on furosemide pharmacokinetics.

Pharmacodynamic Results:

Single doses produced similar peak effects in urine flow with $t_{max}$ approximately 1.5 h after administration of VPA-985 (8.4 mL/min) and furosemide (9.3 mL/min). After their coadministration, the peak urine flow effects increased to 13.3 mL/min. During the 0 to 4 h interval mean urine volumes were 1157 mL (VPA-985), 1524 mL (furosemide), and 2010 mL (VPA-985 with furosemide). Mean 0 to 24 h urine outputs were similar for all treatments. The 0 to 4 h urinary excretion of sodium, potassium, chloride and magnesium was significantly less with VPA-985 alone than with VPA-985 and furosemide administered concomitantly. No differences were observed in 0 to 24 h urinary excretion of potassium or magnesium between furosemide alone and coadministration with VPA-985. Mean serum sodium values 0 to 4 hours after the dose were increased by 2 mmol/L with VPA-985 alone and 3 mmol/L with furosemide administered concomitantly. VPA-985 did not alter serum potassium. A significant decrease in serum potassium was observed after furosemide alone (from 4.2 mmol/L at 0 h to 3.9 mmol/L at 4 hours after the dose), but the decrease was less after coadministration with VPA-985 (from 4.1 mmol/L at 0 hour to 4.0 =mol/L at 4 hours post dose. A similar trend was observed with serum chloride.

These pharmacodynamic results indicate that furosemide administered with VPA-985 increases urine flow and still maintains some electrolyte-sparing capabilities. Therefore, the co-administration of these agents may be used in treatment of physiological states requiring the elimination of excess water without increasing the risk of hyponatremia and hypokalemia.

This invention also includes a pharmaceutical composition comprising a pharmaceutically effective amount of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof, a pharmaceutically effective amount of a diuretic, and a pharmaceutically acceptable carrier or excipient. Preferred embodiments of the pharmaceutical compositions comprise the list of diuretics, above. More preferred pharmaceutical compositions of this invention include VPA-985 and one or more of the loop diuretics referenced above, particularly including furosemide. These pharmaceutical compositions preferably comprise VPA-985 in the pharmaceutical doses described above and the doses of diuretics described herein and those known as effective in the art.

In some cases it may be desirable to have the dose of VPA-985 and the diuretic in separate dosage forms, such as separate tablets or capsules. For such instances, this invention also provides a pharmaceutically useful package or kit adapted for administration of the VPA-985 dosage form(s) and the diuretic dosage form(s), the kit comprising one or more units, preferably daily dosage units, of VPA-985 and one or more units, preferably daily dosage units comprising one or more diuretics, preferably selected from the group of loop diuretics described herein. In one preferred embodiment, the number of dosage units of the two components would be the same.

In a preferred embodiment, a package or kit of this invention would comprise from 1 to 30 dosage units, preferably daily dosage units, of VPA-985 at a concentration of from about 25 mg to about 400 mg per dosage unit, preferably from about 40 mg to about 200 mg per dosage unit, most preferably between about 50 mg and about 150 mg per dosage unit, and from 1 to 30 dosage units, preferably daily dosage units, of a corresponding diuretic at a concentration as described herein or as known in the art. Preferred embodiments of packages or kits of this invention comprises those kits described above in combination with dosage units of a loop diuretic at concentrations described herein for daily administration. A more preferred set of kits herein comprises the combination of VPA-985, or a salt thereof, and furosemide.

Specific non-limiting examples of oral formulations for delivering VPA-985 useful within the scope of this invention are provided below.

EXAMPLE 1

50 mg/capsule: VPA-985 Oral Formulation at 10% Drug Loading

In place of the polysorbate 80 in this formulation of Example 1, other polysorbate series such as Tween 20, 40 and 60 can also be used, alone or in combination with each other and/or polysorbate 80.

| | (% w/w) | per capsule (mg) | 20,000 capsule batch (g) |
|---|---|---|---|
| Active Ingredient: | | | |
| VPA-985 @ 100% | 10.42 | 50.00 | 1000.00 |
| Inactive Ingredients: | | | |
| PEG 1000, NF | 30.96 | 148.61 | 2,972.16 |
| Povidone USP K-17 | 10.00 | 48.00 | 960.00 |
| Polysorbate 80, NF | 10.00 | 48.00 | 960.00 |
| BHT, NF | 0.09 | 0.42 | 8.32 |
| BHA, NF | 0.87 | 4.16 | 83.2 |
| PEG 400, NF[2] | Q.S. to 100 | Q.S. to 480.00 | Q.S. to 9,600 |

1. Weigh the Polysorbate 80, PEG 400, and PEG 1000 into a suitable mixing vessel, stir using a top mounted mixer, and warm to 85±5° C.
2. Add BHT and BHA to the mixing vessel, very slowly to prevent formation of lumps. Continue stirring at 85±5° C., until a clear solution was formed.
3. Add VPA-985 to the vessel at 85±5° C., very slowly to prevent formation of lumps. Slowly raise the temperature to 125±5° C., and stir until VPA-985 dissolves completely.
4. Cool the solution in step 4. to 60±5° C.
5. Add Povidone, USP, K-17 (Plasdone C-15, ISP) slowly to step 5, to prevent the formation of lumps.

Let the solution warm up to 85±5° C. Stir until the solution becomes clear.

6. Encapsulate 480 mg of the finished solution (in step 10) into size 1 capsules at 38±5° C. using either soft or hard gelatin capsule filler. During encapsulation cool the body of capsule using cool Nitrogen to prevent leaking.
7. Band seal the capsules with gelatin solution (optional).

EXAMPLE 2

50 mg/capsule: VPA-985 Oral Formulation at 10% Drug Loading

In place of surfactant used in this formulation (poloxamer 188), other polymers in the series such as Pluronic L44, Pluronic L101 can also be used.

| | (% w/w) | per capsule (mg) | 20,000 capsule batch (g) |
|---|---|---|---|
| Active Ingredient: | | | |
| VPA-985 @ 100% | 10.42 | 50.00 | 1000.00 |
| Inactive Ingredients: | | | |
| Povidone USP K-17 (Plasdone C-15, ISP) | 10.00 | 48.00 | 960.00 |
| Poloxamer 188, NF | 12.00 | 57.60 | 1152.00 |
| BHT NF | 0.09 | 0.42 | 8.32 |
| BHA NF | 0.87 | 4.16 | 83.20 |
| PEG 400 NF | Q.S. to 100 | Q.S. to 480.00 | Q.S. to 9600 g |

This formulation is manufactured the same as that of the formula of Example 1 (50 mg/capsule) with the exception that 12% of poloxamer was used in place of the polysorbate 80 in this formulation. The encapsulation weight is 480 mg.

EXAMPLE 3

50 mg/Capsule

Example 4 provides a formulation with a combination of two or more surfactants.

| | (% w/w) | per capsule (mg) | 20,000 capsule batch (g) |
|---|---|---|---|
| Active Ingredient: | | | |
| VPA-985 @ 100% | 10.64 | 51.07 | 1,021.44 |
| Inactive Ingredient: | | | |
| PEG 1000, NF | 28.60 | 137.28 | 2,745.60 |
| Povidone USP K-17 (Plasdone C-15, ISP) | 10.00 | 48.00 | 960.00 |
| Polysorbate 40, NF | 5.00 | 24.00 | 480.00 |
| Poloxamer 188, NF | 10.00 | 48.00 | |
| BHT, NF | 0.09 | 0.43 | 8.64 |
| BHA, NF | 0.87 | 4.18 | 83.52 |
| PEG 400, NF | Q.S. to 100 | Q.S. to 480.00 | Q.S. to 9600.00 |

The formulation of Example 3 is manufactured the same as that of Example 1 (50 mg/capsule) with the exception that two surfactants, polysorbate 40 and poloxamer 188 were added in step 1 along with PEG 400 and PEG 1000. The encapsulation weight is 480 mg.

EXAMPLE 4

25 mg/Capsule: VPA-985 Oral Formulation at 5% Drug Loading

| | (% w/w) | per capsule (mg) | 20,000 capsule batch (g) |
|---|---|---|---|
| Active Ingredient: | | | |
| VPA-985 @ 100% | 5.49 | 25.00 | 500.00 |
| Inactive Ingredient: | | | |
| PEG 1000, NF | 32.66 | 148.61 | 2,972.16 |
| Povidone, USP K-17 (Plasdone C-15, ISP) | 10.55 | 48.00 | 960.00 |
| Polysorbate 80, NF | 10.55 | 48.00 | 960.00 |
| BHT, NF | 0.09 | 0.42 | 8.32 |
| BHA, NF | 0.91 | 4.16 | 83.2 |
| PEG 400, NF[2] | Q.S. to 100 | Q.S. to 455.00 | Q.S. to 9,100 g |

The formulation of Example 4 is produced in the same manner as that of 50 mg/capsule, above, with the exception that the heating temperature to solubilize VPA-985 in step 3 is 115±5° C., instead of 120±5° C. The encapsulation weight is 455 mg.

EXAMPLE 5

100 mg/Capsule: VPA-985 Oral Formulation at 15% Drug Loading

| | (% w/w) | per capsule (mg) | 20,000 capsule batch (g) |
|---|---|---|---|
| Active Ingredient: | | | |
| VPA-985 @ 100% | 15.38 | 100.00 | 2,000.00 |
| Inactive Ingredient: | | | |
| PEG 1000, NF | 28.98 | 188.35 | 3,767.05 |
| Povidone USP K-17 (Plasdone C-15, ISP)[3] | 10.00 | 65.00 | 1,300.00 |
| Polysorbate 80, NF | 9.45 | 61.39 | 1,227.91 |
| BHT, NF | 0.08 | 0.53 | 10.64 |
| BHA, NF | 0.82 | 5.32 | 106.42 |
| PEG 400, NF | Q.S. to 100 | Q.S. to 650.00 | Q.S. to 13,000.00 |

This formulation is produced with the same steps as the 50 mg/capsule, above, with the exception that the heating temperature to solubilize VPA-985 in step 3 is 145±5° C., instead of 120±5° C. The encapsulation weight is 650 mg in size 0 hard gelatin capsule.

EXAMPLE 6

VPA-985: 150 mg in Size 00 Capsule

| | (% w/w) | per capsule (mg) | 20,000 capsule batch (g) |
|---|---|---|---|
| Active Ingredient: | | | |
| VPA-985 @ 100% | 16.48 | 149.97 | 2,999.36 |
| Inactive Ingredients: | | | |
| PEG 1000, NF | 26.3 | 239.33 | 4,786.60 |
| Povidone USP K-17 (Plasdone C-15, ISP) | 15 | 136.50 | 2,730.00 |
| Polysorbate 80, NF | 9.32 | 84.81 | 1,696.24 |
| BHT, NF | 0.08 | 0.73 | 14.56 |
| BHA, NF | 0.81 | 7.37 | 147.42 |
| PEG 400, NF | Q.S. to 100 | Q.S. to 910.00 | Q.S. to 18,200.00 |

This formulation of Example 6 is produced with the same steps as that of 50 mg/capsule with the exception of the heating temperature to solubilize VPA-985 in step 3 is 150±5° C., instead of 145±5° C. The encapsulation weight is 910 mg in size 00 hard gelatin capsule.

The following specific Examples 7 through 11 shown in Table 1, below, were formulated as described above to create formulations of 10% N-[4-(5H-pyrrolo[2,1-c][1,4]benzodiazepin-10(11H)ylcarbonyl)-3-chlorophenyl]-5-fluoro-2-methyl-benzamide (VPA-985) with varying concentrations of PEG 400, PEG 1000, two PVP components with respective K values of 15 and 90, and a combination of BHA and BHT as an adjuvant component.

TABLE 1

| Example No. | PEG 400 (%) | PEG 1000 (%) | PVP K15 (%) | PVP K90 (%) | BHT (%) | BHA (%) | NATC (%) | VPA-985 (%) |
|---|---|---|---|---|---|---|---|---|
| 7 | 55.40 | 20.00 | 10.00 | 0.00 | 0.20 | 2.00 | 2.40 | 10.00 |
| 8 | 40.40 | 35.00 | 10.00 | 0.00 | 0.20 | 2.00 | 2.40 | 10.00 |

TABLE 1-continued

| Example No. | PEG 400 (%) | PEG 1000 (%) | PVP K15 (%) | PVP K90 (%) | BHT (%) | BHA (%) | NATC (%) | VPA-985 (%) |
|---|---|---|---|---|---|---|---|---|
| 9 | 75.40 | 0.00 | 5.00 | 5.00 | 0.20 | 2.00 | 2.40 | 10.00 |
| 10 | 65.40 | 10.00 | 0.00 | 10.00 | 0.20 | 2.00 | 2.40 | 10.00 |
| 11 | 40.40 | 35.00 | 5.00 | 5.00 | 0.20 | 2.00 | 2.40 | 10.00 |

Similarly, the following Examples 12 through 32 were formulated by the methods herein using PEG 400, PEG 1000, PVP with a K value of 17, VPA-985, BHA and BHT as antioxidants or preservatives and the additional components listed as "other".

TABLE 2

| Ex. No. | PEG 400 | PEG 1000 | PVP K-17 | VPA-985 | BHA | BHT | Other | Other |
|---|---|---|---|---|---|---|---|---|
| 12 | 40.40 | 35.00 | 10.00 | 10.00 | 2.00 | 0.20 | Sodium Taurocholate 2.40 | — |
| 13 | 75.40 | — | 5.00 | 10.21 | 2.00 | 0.20 | Sodium Taurocholate 2.40 | PVP K-90 5.00 |
| 14 | 42.59 | 35.00 | 10.00 | 10.21 | 2.00 | 0.20 | — | — |
| 15 | 34.35 | 28.23 | 10.00 | 10.21 | 2.00 | 0.20 | Poloxamer 188 15.00 | — |
| 16 | 42.59 | 20.00 | 10.00 | 10.21 | 2.00 | 0.20 | Poloxamer 188 15.00 | — |
| 17 | 37.10 | 30.49 | 10.00 | 10.21 | 2.00 | 0.20 | Poloxamer 188 10.00 | — |
| 18 | 35.72 | 29.36 | 10.00 | 10.21 | 2.00 | 0.20 | Poloxamer 188 12.50 | — |
| 19 | 34.35 | 28.23 | 10.00 | 10.21 | 2.00 | 0.20 | Poloxamer 188 15.00 | — |
| 20 | 37.10 | 30.49 | 10.00 | 10.21 | 2.00 | 0.20 | Poloxamer 188 10.00 | — |
| 21 | 34.35 | 28.23 | 10.00 | 10.21 | 2.00 | 0.20 | Poloxamer 188 15.00 | — |
| 22 | 35.72 | 29.36 | 10.00 | 10.21 | 2.00 | 0.20 | Poloxamer 188 12.50 | — |
| 23 | 36.86 | 30.30 | 10.00 | 10.64 | 2.00 | 0.20 | Pluronic L44 10.00 | — |
| 24 | 36.86 | 30.30 | 10.00 | 10.64 | 2.00 | 0.20 | Pluronic L101 10.00 | — |
| 25 | 39.61 | 32.55 | 10.00 | 10.64 | 2.00 | 0.20 | Tween 40 5.00 | — |
| 26 | 41.25 | 33.91 | 10.00 | 10.64 | 2.00 | 0.20 | Tween 40 2.00 | — |
| 27 | 39.61 | 32.55 | 10.00 | 10.64 | 2.00 | 0.20 | Tween 20 5.00 | — |
| 28 | 41.25 | 33.91 | 10.00 | 10.64 | 2.00 | 0.20 | Tween 20 2.00 | — |
| 29 | 34.12 | 28.04 | 10.00 | 10.64 | 2.00 | 0.20 | Tween 40 5.00 | Poloxamer 188 10.00 |
| 30 | 36.86 | 30.30 | 10.00 | 10.64 | 2.00 | 0.20 | Tween 40 | — |
| 31 | 36.86 | 30.30 | 10.00 | 10.64 | 2.00 | 0.20 | Tween 80 10.00 | — |
| 32 | 34.12 | 28.04 | 10.00 | 10.64 | 2.00 | 0.20 | Tween 80 5.00 | Poloxamer 188 10.00 |

EXAMPLE 33

25 mg/Capsule in Size #3 Capsule: VPA-985 Oral Formulation at 10% Drug Loading

In place of the polysorbate 80, other polysorbate series such as Tween 20, 40 and 60 can also be used.

|  | (% w/w) | per capsule (mg) | 20,000 capsule batch (g) |
|---|---|---|---|
| Active Ingredient: | | | |
| VPA-985 @ 100% | 10.42 | 25 | 500.00 |
| Inactive Ingredients: | | | |
| PEG 1000, NF | 30.96 | 74.31 | 1,486.08 |
| Povidone USP K-17 | 10.00 | 24.00 | 480.00 |
| Polysorbate 80, NF | 10.00 | 24.00 | 480.00 |
| BHT, NF | 0.09 | 0.21 | 4.16 |
| BHA, NF | 0.87 | 2.08 | 41.6 |
| PEG 400, NF[2] | Q.S. to 100 | Q.S. to 240 | Q.S. to 4800 |

What is claimed:

1. A pharmaceutical composition comprising a pharmaceutically effective amount of N-[4-(5H-pyrrolo[2,1-c][1,4]benzodiazepin-10(11H)ylcarbonyl)-3-chlorophenyl]-5-fluoro-2-methylbenzamide or a pharmaceutically acceptable salt thereof, a pharmaceutically effective amount of a Loop diuretic agent, and a pharmaceutically acceptable carrier or excipient.

2. The pharmaceutical composition of claim 1 wherein the diuretic agent is selected from the group consisting of bumetanide, ethacrynic acid, ethacrynate sodium, and furosemide.

3. The pharmaceutical composition of claim 1 wherein the diuretic agent is furosemide.

4. The pharmaceutical composition claim 3 wherein the pharmaceutically effective amount of furosemide is between from about 20 mg to about 100 mg.

5. The pharmaceutical composition of claim 1 wherein the pharmaceutically effective amount of N-[4-(5H-pyrrolo[2,1-c][1,4]benzodiazepin-10(11H)ylcarbonyl)-3-chlorophenyl]-5-fluoro-2-methylbenzamide is between from about 25 mg to about 400 mg.

6. The pharmaceutical composition of claim 1 wherein the pharmaceutically effective amount of N-[4-(5H-pyrrolo[2,1-c][1,4]benzodiazepin-10(11H)ylcarbonyl)-3-chlorophenyl]-5-fluoro-2-methylbenzamide is between from about 50 mg to about 150 mg.

7. A kit comprising one or more dosage units of N-[4-(5H-pyrrolo[3,1-c][1,4]benzodiazepin-10(11H)ylcarbonyl)-3-chlorophenyl]-5-fluoro-2-methylbenzamide, or a pharmaceutically acceptable salt thereof, and one or more dosage units of a Loop diuretic agent.

8. The kit of claim 7 wherein the diuretic agent is selected from the group consisting of bumetanide, ethacrynic acid, ethacrynate sodium, and furosemide.

9. The kit of claim 7 comprising from one to thirty dosage units of N-[4-(5H-pyrrolo[2,1-c][1,4]benzodiazepin-10(11H)ylcarbonyl)-3-chlorophenyl]-5-fluoro-2-methylbenzamide, or a pharmaceutically acceptable salt thereof, and from one to thirty dosage units of a diuretic agent selected from the group consisting of bumetanide, ethacrynic acid, ethacrynate sodium, and furosemide.

* * * * *